(12) United States Patent
Malik et al.

(10) Patent No.: US 9,573,896 B2
(45) Date of Patent: *Feb. 21, 2017

(54) METHODS FOR PREPARING D-THREO-METHYLPHENIDATE USING DIAZOMETHANE, AND COMPOSITIONS THEREOF

(71) Applicant: AMPAC Fine Chemicals LLC, Rancho Cordova, CA (US)

(72) Inventors: Aslam Malik, Cameron Park, CA (US); Francis Hempenstall, Folsom, CA (US); Nicholas Duda, Orangevale, CA (US); Ali Suleman, Folsom, CA (US)

(73) Assignee: AMPAC Fine Chemicals LLC, Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,416

(22) Filed: Dec. 4, 2015

(65) Prior Publication Data

US 2016/0090356 A1    Mar. 31, 2016

Related U.S. Application Data

(62) Division of application No. 14/204,257, filed on Mar. 11, 2014, now Pat. No. 9,233,924.

(51) Int. Cl.
*C07D 211/34* (2006.01)
*A61K 31/4458* (2006.01)
*B01J 19/24* (2006.01)

(52) U.S. Cl.
CPC ......... *C07D 211/34* (2013.01); *A61K 31/4458* (2013.01); *B01J 19/24* (2013.01); *B01J 2219/00051* (2013.01); *B01J 2219/24* (2013.01)

(58) Field of Classification Search
CPC .................................................. C07D 211/34
USPC ......................................................... 546/238
See application file for complete search history.

(56) References Cited

U.S. PATENT DOCUMENTS

| 2,838,519 | A | 6/1958 | Rometsch |
| 2,957,880 | A | 10/1960 | Rometsch |
| 5,817,778 | A | 10/1998 | Archibald et al. |
| 5,854,405 | A | 12/1998 | Archibald et al. |
| 5,965,734 | A | 10/1999 | Ramaswamy et al. |
| 9,233,924 | B2* | 1/2016 | Malik ................ C07D 211/34 |

FOREIGN PATENT DOCUMENTS

| WO | 9825902 A1 | 6/1998 |
| WO | 9852921 A1 | 11/1998 |

OTHER PUBLICATIONS

Patrick et al, "Pharmacology fo the Enantiomers of threo-Methylphenidate," Journal of Pharmacology and Experimental Therapeutics, vol. 241, No. 1, pp. 152-158 (1987).
Prashad et al, "Enzymatic resolution of (+−)-threo-methylphenidate," Tetraherdron: Asymmetry, vol. 9, pp. 2133-2136 (1998).
Thai et al, "Asymmetric Synthesis and Pharmacology of Methylphenidate and Its Para-Substituted Derivatives," J. Med. Chem., vol. 41, pp. 591-601 (1998).
Berge et al, "Pharmaceutical Salts," Journal of Pharmaceutical Sciences, vol. 66, No. 1, pp. 1-19 (Jan. 1977).
Forro et al. Tetrahedron: Asymmetry 17 (2006) p. 3193-3196.

* cited by examiner

*Primary Examiner* — Nizal Chandrakumar
(74) *Attorney, Agent, or Firm* — Panitch Schwarze Belisario & Nadel LLP

(57) ABSTRACT

Novel methods and systems for producing a substantially pure d-threo stereoisomer of methylphenidate or a salt thereof are provided. In particular, methods and systems for producing d-threo-methylphenidate hydrochloride in pure stereoisomeric form from d-threo-ritalinic acid hydrochloride using diazomethane are described. The described methods can be performed on a large scale, and thus provide d-threo methylphenidate or a salt thereof, and particularly the hydrochloride salt of d-threo-methylphenidate, in stereoisomerically pure form and in large quantities from a single batch reaction. Also described are novel compositions of d-threo methylphenidate hydrochloride.

13 Claims, No Drawings

METHODS FOR PREPARING D-THREO-METHYLPHENIDATE USING DIAZOMETHANE, AND COMPOSITIONS THEREOF

CROSS-REFERENCE TO RELATED APPLICATION

This application is a Divisional of U.S. patent application Ser. No. 14/204,257, filed Mar. 11, 2014, and the disclosure of which is incorporated herein by reference in its entirety.

FIELD OF THE INVENTION

The present invention relates to a method for producing a substantially pure d-threo stereoisomer of methylphenidate or a salt thereof by converting a carboxylic acid group on a substantially pure d-threo stereoisomer of ritalinic acid or a salt thereof to an ester group using diazomethane, and compositions thereof. In particular, the present invention relates to a method for producing substantially pure d-threo-methylphenidate hydrochloride by reacting substantially pure d-threo-ritalinic acid hydrochloride with diazomethane. Methods according to the present invention can be used to produce the target compound in large quantities.

BACKGROUND OF THE INVENTION

Substituted piperidine compounds have been used in the treatment of many nervous system disorders. One particular substituted piperidine compound proven useful in treating central nervous system disorders is dexmethylphenidate, which is often prescribed to control symptoms of attention deficit hyperactivity disorder (ADHD).

Dexmethylphenidate, also referred to as d-threo-methylphenidate and (2R,2'R)-(+)-threo-methylphenidate, is the d-threo stereoisomer of methylphenidate. Methylphenidate exists in four stereoisomeric forms: d-threo, l-threo, d-erythro and l-erythro. d-threo-methylphenidate and l-threo-methylphenidate are enantiomers, and l-erythro-methylphenidate and d-erythro-methylphenidate are enantiomers. However, preparing and isolating dexmethylphenidate in its pure stereoisomeric form, i.e., the d-threo stereoisomer, has proven to be difficult.

The preparations of enantiomerically pure dexmethylphenidate hydrochloride were reported by R. Rometsch in U.S. Pat. Nos. 2,838,519 and 2,957,880. According to the methods described by Rometsch, enantiomerically pure l-erytho-2-phenyl-2-(2-piperidyl)acetamide was first obtained by resolution of a racemic mixture of erythro-2-phenyl-2-(2-piperidyl)acetamide with d-(±)-tartaric acid in 96% ethanol. The enantiomerically pure l-erythro-2-phenyl-2-(2-piperidyl)acetamide was epimerized in aqueous potassium hydroxide to the d-threo-2-phenyl-2-(2-piperidyl)acetamide stereoisomer. d-threo-methylphenidate hydrochloride was then obtained upon hydrolysis and esterification of d-threo-2-phenyl-2-(2-piperidyl)acetamide.

The initial approach described by Rometsch was further optimized by Khetani et al. in PCT Patent Application Publication No. WO 98/52921 and Ramaswamy et al. in U.S. Pat. No. 5,965,734. Resolution of a racemic mixture of erythro-2-phenyl-2-(2-piperidyl)acetamide with d-(±)-tartaric acid in methanol afforded a 40% yield of l-erythro-2-phenyl-2-(2-piperidyl)acetamide. Epimerization of l-erythro-2-phenyl-2-(2-piperidyl)acetamide with potassium tert-butoxide in toluene at 70° C. furnished d-threo-2-phenyl-2-(2-piperidyl)acetamide in 85% yield. d-threo-2-phenyl-2-(2-piperidyl)acetamide was converted to d-threo-methylphenidate hydrochloride upon treatment with concentrated sulfuric acid in refluxing methanol and hydrochloride salt in 80% yield.

Further, several methods have been reported for enriching the enantiomeric purity of dexmethylphenidate, with the first method being reported in 1987 by Patrick et al. *J. Pharm. Exp. Ther.* (1987) 241, 152-158, by crystallization of dexmethylphenidate from a mixture of methanol and ether. Novartis also reportedly increased the enantiomeric purity of dexmethylphenidate hydrochloride from 80% enantiomeric excess (e.e.) to greater than 98% e.e. by recrystallization from a 1:1.7 (v/v) mixture of methanol and t-butyl methyl ether (M. Prashad et al., *Tetrahedron: Asymmetry* (1998) 9, 2133-2136). PCT Patent Application Publication WO 98/25902 also reports an enrichment of the enantiomeric purity of dexmethylphenidate hydrochloride from this same solvent mixture. Although such attempts to enrich the enantiomeric purity of dexmethylphenidate hydrochloride by recrystallization do provide enantiomerically pure compound, recrystallization results in loss of yield and is not desirable for use with reactions that are performed on a large scale to obtain large quantities of the desired product.

An alternative approach to synthesizing enantiomerically pure d-threo-methylphenidate hydrochloride using an enantiomerically pure starting material, d-pipecolic acid, was reported by Thai et al. in *J. Med. Chem.* (1998) 41, 591-601. Enantiomerically pure d-pipecolic acid was obtained in 37% yield by recrystallization of the diastereomeric tartrate salt, followed by the separation of the desired amino acid from tartaric acid by ion-exchange chromatography. d-pipecolic acid was protected with a BOC group to afford N-BOC-d-pipecolic acid in 97% yield. The key amino ketone was prepared from N-BOC-d-pipecolic acid in two steps involving its conversion to the N-methoxy-N-methyl amide, followed by a reaction with the amide with phenyllithium. The amino ketone underwent a Wittig olefination with methyltriphenylphosphonium bromide in the presence of potassium tert-butoxide to give the alkene in high yield. The transformation of the obtained alkene to the desired alcohol as a racemic mixture of threo-stereoisomers via a hydroboration/oxidation reaction was critical to introducing the second stereogenic center. Hydroboration with $BH_3$-THF gave a 72:28 mixture of threo and erythro isomers, respectively, from which the threo alcohol was isolated in 64% yield after chromatography. Oxidation of the threo alcohol with pyridinium dichromate (PDC) in dimethylformamide (DMF) followed by esterification of the resulting acid with diazomethane, and N-BOC group deprotection with 3 N methanolic hydrochloric acid furnished d-threo-methylphenidate hydrochloride in 67% yield after recrystallization from a mixture of ethanol and ether.

However, all of the aforementioned methods for obtaining dexmethylphenidate in its pure enantiomeric form require either recrystallization from a mixture of stereoisomers, or a large number of synthetic steps, both of which result in reduced yields. Thus, there is a need for improved methods of preparing dexmethylphenidate in its pure enantiomeric form and in high yield. Preferably, such methods are also adaptable to production on a large scale, which would have the advantage of providing a method for obtaining dexmethylphenidate in its pure enantiomeric form and in large quantities from a single reaction.

BRIEF SUMMARY OF THE INVENTION

The present invention is directed to methods for preparing d-threo methylphenidate in enantiomerically pure form in large quantities as compared to other methods known in the art for preparing such compounds. In particular, the present invention relates to methods for preparing a substantially pure d-threo methylphenidate or a salt thereof, and preferably d-threo-methylphenidate hydrochloride, by a reaction that employs diazomethane. Methods according to the present invention can be performed on a large scale, and thus provide stereoisomerically pure compound in large quantities from a single batch reaction.

In one general aspect, the present invention relates to a method for preparing a substantially pure d-threo stereoisomer of methylphenidate represented by formula (I):

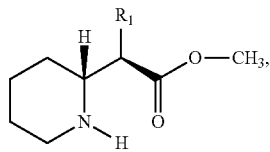

(I)

or a salt thereof represented by formula (I-a):

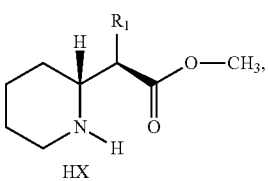

(I-a)

the method comprising:
  (i) obtaining a first solution comprising an aqueous solution of an inorganic base and a water miscible solvent;
  (ii) obtaining a second solution comprising an N-methyl-N-nitroso amine of formula (IV):

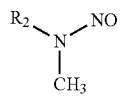

(IV)

in a water immiscible organic solvent;
  (iii) adding the second solution to the first solution, thereby generating diazomethane; and
  (iv) reacting a substantially pure d-threo stereoisomer of ritalinic acid represented by formula (II):

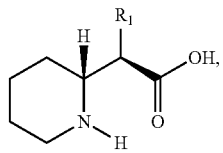

(II)

or a salt thereof represented by formula (II-a):

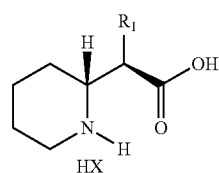

(II-a)

with the diazomethane generated in step (iii) to obtain the substantially pure d-threo stereoisomer of methylphenidate or salt thereof,
wherein $R^1$ represents a phenyl group; $R^2$ represents a member selected from the group consisting of

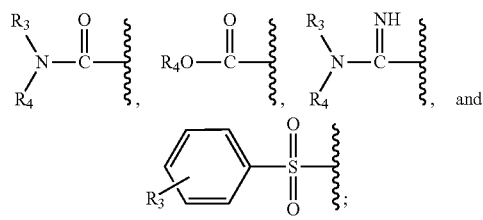

$R_3$ represents a hydrogen atom, an alkyl group having one to four carbon atoms, or a nitro group; $R_4$ represents a hydrogen atom or an alkyl group having one to four carbon atoms; and X represents fluorine, chlorine, bromine, iodine, or tetrafluoroborate.

In another general aspect, the present invention provides a method for preparing substantially pure d-threo-methylphenidate hydrochloride, the method comprising:
  (i) obtaining a first solution comprising an aqueous solution of an inorganic base and a water miscible solvent;
  (ii) obtaining a second solution comprising an N-methyl-N-nitroso amine of formula (IV):

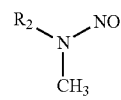

(IV)

in a water immiscible organic solvent;
  (iii) adding the second solution to the first solution, thereby generating diazomethane; and
  (iv) reacting substantially pure d-threo-ritalinic acid hydrochloride with the diazomethane generated in step (iii) to obtain the substantially pure d-threo-methylphenidate hydrochloride,
wherein $R^2$ represents a member selected from the group consisting of

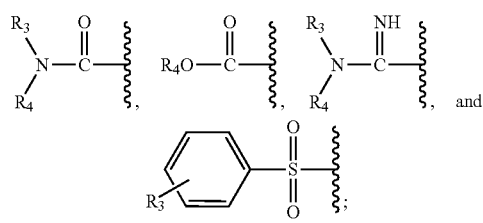

$R_3$ represents a hydrogen atom, an alkyl group having one to four carbon atoms, or a nitro group; and $R_4$ represents a hydrogen atom or an alkyl group having one to four carbon atoms.

In yet another general aspect, the present invention relates to a system for producing a substantially pure d-threo stereoisomer of methylphenidate represented by formula (I):

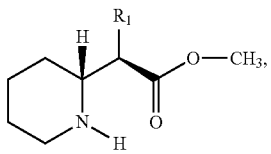

or a salt thereof represented by formula (I-a):

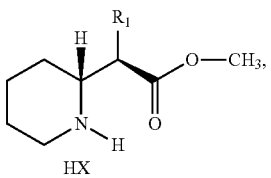

the system comprising:
(i) a reaction chamber comprising:
  (a) a generator portion comprising an inlet, and holding an aqueous solution comprising an inorganic base and a water miscible solvent, and
  (b) a receiver portion connected to the generator portion by a condenser, the receiver portion holding a substantially pure d-threo stereoisomer of ritalinic acid represented by formula (II):

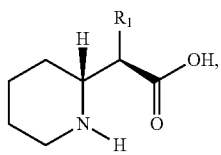

or a salt thereof represented by formula (II-a):

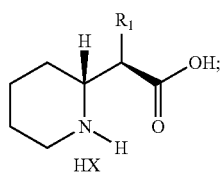

and
(ii) a solution of an N-methyl-N-nitroso amine of formula (IV):

in a water immiscible organic solvent,
wherein the generator portion is maintained at a temperature sufficient to vaporize the organic solvent and any diazomethane that is formed upon introduction of the solution of the N-methyl-N-nitroso amino of formula (IV) into the generator portion via the inlet; $R^1$ represents a phenyl group; $R^2$ represents a member selected from the group consisting of

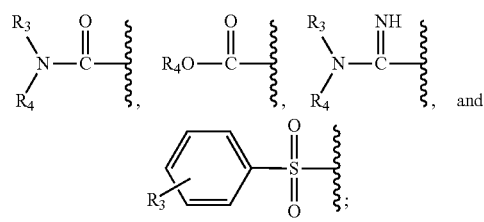

$R_3$ represents a hydrogen atom, an alkyl group having one to four carbon atoms, or a nitro group; and $R_4$ represents a hydrogen atom or an alkyl group having one to four carbon atoms; and X represents fluorine, chlorine, bromine, or tetrafluoroborate.

In a preferred embodiment, the present invention provides a system for producing substantially pure d-threo-methylphenidate hydrochloride, such that the receiver portion of the reaction chamber holds substantially pure d-threo ritalinic acid hydrochloride.

The invention also relates to compositions comprising substantially pure d-threo-methylphenidate hydrochloride and an N-methyl species of d-threo methylphenidate hydrochloride. Preferably, the composition contains the N-methyl species of d-threo methylphenidate hydrochloride present in amount that is no more than 0.10% area based on peak area of a peak corresponding to the N-methyl species as determined by high performance liquid chromatography (HPLC) analysis relative to a total of 100% area based on peak area of peaks corresponding to the substantially pure d-threo-methylphenidate hydrochloride and N-methyl species thereof as determined by HPLC analysis.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

The term "halogen," as used herein, refers to an atom of fluorine, bromine, chlorine or iodine.

As used herein, the term "stereoisomers" refers to at least two compounds having the same molecular formula and connectivity of atoms, but having a different arrangement of atoms in a three-dimensional space. A stereoisomer often, but not exclusively has a chiral carbon atom. As used herein, a "chiral carbon atom" is a carbon atom in which four different atoms or four different groups of atoms are attached. Compounds containing chiral carbon atoms typically, but not always, rotate the plane of polarized light, and are thus referred to as being "optically active."

As used herein, the term "substantially pure stereoisomer" when referring to a compound that has multiple stereoisomers, means that the compound exists as a single stereoisomer that is substantially free of the other stereoisomers of that compound, but not necessarily free of other materials. As used herein, the term "substantially pure d-threo stereoisomer," when referring to a compound that has d-threo, l-threo, d-erythro, and l-erythro stereoisomers, means that the compound exists as a d-threo stereoisomer that is substantially free of the l-threo, d-erythro, and l-erythro stereoisomers, but not necessarily free of other materials. As used herein, "substantially pure d-threo-methylphenidate" refers to the d-threo stereoisomer of methylphenidate that is substantially free of the l-threo, d-erythro, and l-erythro stereoisomers, but not necessarily free of other materials. As used herein, "substantially pure d-threo ritalinic acid" refers to the d-threo stereoisomer of ritalinic acid that is substantially free of the l-threo, d-erythro, and l-erythro stereoisomers, but not necessarily free of other materials.

As used herein, a "water immiscible organic solvent" is any organic solvent that forms a separate phase when contacted with water. A water immiscible solvent according to the invention can be an organic solvent that is fully immiscible with water, meaning that it is incapable of being mixed with water to form a homogenous solution. A water immiscible solvent according to the invention can also be an organic solvent that is partially immiscible with water, as long as the organic solvent forms a second phase when contacted with water. Examples of water immiscible organic solvents that can be used in the invention include, but are not limited to, ethers, such as diethyl ether, methyl ethyl ether, and methyl propyl ether; alkanes, such as hexanes and heptanes; and hydrocarbon mixtures. Preferably, the water immiscible organic solvent is an ether, and most preferably is diethyl ether.

As used herein, a "water miscible solvent" refers to any solvent that can form a homogeneous mixture with water when contacted with water. For a solvent to be considered "water miscible," there is little to no phase separation when the solvent is mixed with water. Examples of water miscible solvents include, but are not limited to, water soluble alcohols, such as methanol, ethanol, and propanol; glycols, such as ethylene glycol; acetone; acetonitrile; tetrahydrofuran; dimethylformamide and the like.

As used herein, "a phase transfer catalyst" is any catalyst that will dissolve in a two-phase liquid system and enhance the rate of reaction between a reactant in an aqueous phase and one in an organic phase. A wide variety of phase transfer catalysts are known in the art including, but not limited to, quaternary ammonium or phosphonium salts, crown ethers, and glycols.

As used herein, "methylphenidate" refers to a compound having the following general formula (I):

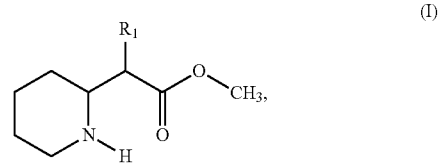

(I)

wherein $R_1$ represents a phenyl group. Methylphenidate has four different stereoisomers:

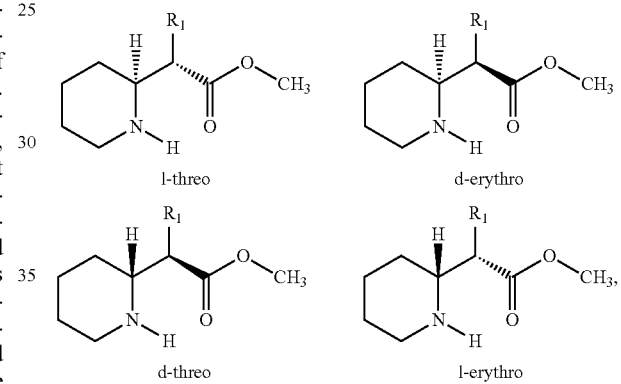

wherein $R_1$ represents phenyl.

As used herein, "d-threo-methylphenidate" is intended to mean the d-threo stereoisomer of methylphenidate, which can also be referred to herein as dexmethylphenidate or (2R,2'R)-(+)-methylphenidate. d-threo-methylphenidate has the following chemical structure:

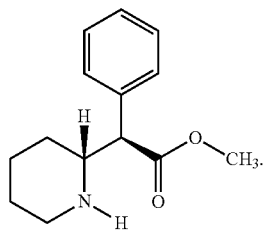 [SMILES: COC(=O)[C@H](c1ccccc1)[C@H]1CCCCN1]

The present invention provides methods for preparing a substantially pure d-threo stereoisomer of methylphenidate or a salt thereof, and preferably substantially pure d-threo-methylphenidate hydrochloride.

In one general aspect, the present invention provides a method for preparing a substantially pure d-threo stereoisomer of methylphenidate represented by formula (I):

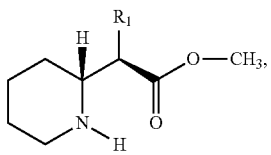

or a salt thereof represented by formula (I-a):

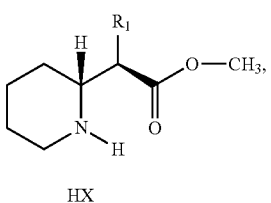

wherein $R_1$ is a phenyl group, and X represents fluorine, chlorine, bromine, iodine, or tetrafluoroborate. A method according to the present invention comprises reacting a substantially pure d-threo ritalinic acid represented by formula (II):

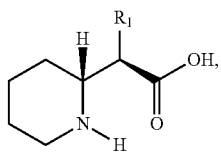

or a salt thereof represented by formula (II-a):

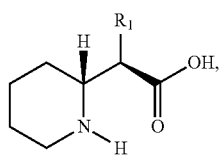

with diazomethane, wherein X and $R_1$ are defined as above.

Diazomethane, which can be abbreviated as $CH_2N_2$, is a methylating reagent used to convert carboxylic acids to methyl esters. It is also used as a methylating reagent for other functional groups, such as phenols, alcohols, and heteroatoms, and for ring expansion or chain extension of ketones. Thus, diazomethane has utility in a wide range of chemical syntheses. However, diazomethane is highly explosive and highly toxic, which limits its use in the production of compounds on a large scale. Thus, despite its applicability in chemical synthesis, diazomethane is often only employed in small scale reactions when it can be used under dilute conditions. In the present invention, it has been discovered that diazomethane can be used in large scale reactions to produce large quantities of a substantially pure d-threo stereoisomer of methylphenidate represented by formula (I), or a salt thereof represented by formula (I-a), and in particular, large quantities of substantially pure d-threo-methylphenidate hydrochloride in a single batch production.

A method for producing a substantially pure d-threo stereoisomer of methylphenidate by reacting a substantially pure d-threo stereoisomer of ritalinic acid with diazomethane according to embodiments of the present invention is depicted in Scheme 1 below. A method for producing a salt of a substantially pure d-threo stereoisomer of methylphenidate by reacting a salt of a substantially pure d-threo stereoisomer of ritalinic acid with diazomethane according to embodiments of the present invention is depicted in Scheme 2 below.

Scheme 1: Production of a substantially pure d-threo stereoisomer of methylphenidate represented by formula (I) using diazomethane.

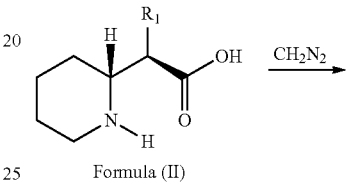

Formula (II)

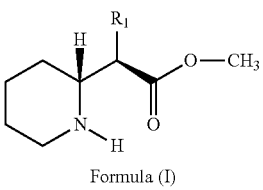

Formula (I)

Scheme 2: Production of a salt of a substantially pure d-threo steroisomer of methylphenidate represented by formula (I-a) using diazomethane.

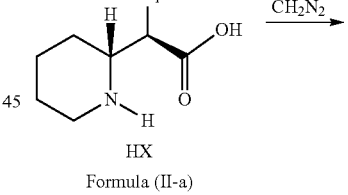

Formula (II-a)

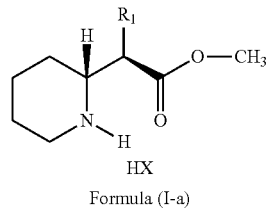

Formula (I-a)

According to embodiments of the present invention, diazomethane can be prepared by any method known in the art and described herein. For example, methods for preparing diazomethane are described in U.S. Pat. Nos. 5,854,405 and 5,817,778, which are incorporated herein by reference in their entirety.

In one embodiment, diazomethane for use in the present invention is prepared by adding a solution of an N-methyl-N-nitroso amine of formula (IV):

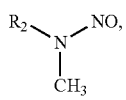

in a water immiscible organic solvent to an aqueous solution comprising an inorganic base and a water miscible solvent, wherein $R_2$ represents a member selected from the group consisting of consisting of:

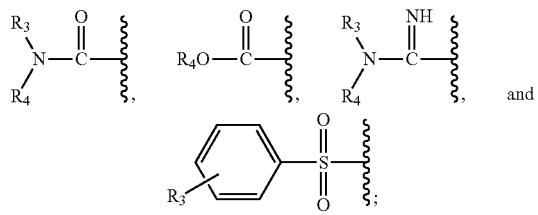

$R_3$ represents a hydrogen atom, an alkyl group having one to four carbon atoms, or a nitro group; and $R_4$ represents a hydrogen atom or an alkyl group having one to four carbon atoms.

Examples of N-methyl-N-nitroso amines of formula (IV) that can be used with the present invention include, but are not limited to, N-methyl-N-nitrosourea, N,N'-dimethyl-N-nitrosourea, N-methyl-N'-nitro-N-nitrosourea, N-methyl-N-nitrosoguanidine, N,N'-dimethyl-N-nitrosoguanidine, N-methyl-N'-nitrosoguanidine, N-methyl-N-nitrosocarbamic acid, N-methyl-N-nitrosocarbamate, methyl N-methyl-N-nitrosocarbamate, ethyl N-methyl-N-nitrosocarbamate, and N-methyl-N-nitroso-p-toluenesulfonamide.

In a preferred embodiment, the N-methyl-N-nitroso amine of formula (IV) is N-methyl-N-nitroso-p-toluenesulfonamide. N-methyl-N-nitroso-p-toluenesulfonamide can by synthesized according to any method known in the art or it can be obtained from commercial sources, e.g., Sigma-Aldrich, which sells N-methyl-N-nitroso-p-toluenesulfonamide under the trade name DIAZALD®. The N-methyl-N-nitroso amine of formula (IV) is prepared as a solution in a water immiscible organic solvent. The water immiscible organic solvent is preferably one that will co-distill with the diazomethane that is produced to decrease the risk of accumulating a high concentration of diazomethane in the vapor phase. In this way, the concentration of diazomethane can be kept below non-explosive levels. Examples of such water immiscible organic solvents include, but are not limited to ethers, diethers, alkanes and hydrocarbon mixtures such as petroleum ethers with boiling temperatures below about 50° C. Preferably the water immiscible organic solvent is an ether solvent, more preferably an ether solvent with a boiling point less than about 40° C., and most preferably is diethyl ether.

According to embodiments of the present invention, a solution of an N-methyl-N-nitroso amine of formula (IV) is prepared in the water immiscible organic solvent. The solution containing the N-methyl-N-nitroso amine is then added at a controlled rate to an aqueous solution comprising an inorganic base and a water miscible solvent. The rate at which the solution containing the N-methyl-N-nitroso amine is added to the aqueous solution is determined based upon the particular reaction parameters including the concentration of N-methyl-N-nitroso amine in the water-immiscible organic solvent, the specific water-immiscible organic solvent that is used, and the concentration of base in the aqueous solution.

The inorganic base in the aqueous solution is not limited in any way and can be, for example, an alkali metal hydroxide, such as lithium hydroxide, sodium hydroxide, and potassium hydroxide. A preferred inorganic base is potassium hydroxide.

According to embodiments of the present invention, a phase transfer catalyst can be included in the aqueous solution comprising the inorganic base and the water miscible solvent. The phase transfer catalyst can be any phase transfer catalyst known in the art and described herein. For example, the phase transfer catalyst can be selected from quaternary ammonium salts, quaternary phosphonium salts, crown ethers and glycol ethers. Preferably, the phase transfer catalyst has a high boiling point and does not undergo chemical decomposition or evaporate into the vapor phase under the conditions used to generate the diazomethane, which is under basic conditions at temperatures most often greater than 45° C. Examples of quaternary ammonium salts suitable for use in the present invention include benzyltriethylammonium chloride, methyltrioctylammonium chloride, methyltrioctylammonium bromide, tetra-n-butylammonium chloride, and tetra-n-butylammonium bromide. Examples of quaternary phosphonium salts suitable for use in the present invention include tetra-n-butylphosphonium chloride and tetra-n-butyl-phosphonium bromide. Examples of crown ethers suitable for use in the present invention include hexaoxacyclooctodecane. Preferred phase transfer catalysts include glycol ethers, such as diethylene glycol monomethyl ether, diethylene glycol monoethyl ether, triethylene glycol monomethyl ether, and triethylene glycol monomethyl ether, and is most preferably diethylene glycol monoethyl ether.

According to embodiments of the present invention, when a phase transfer catalyst is included in the aqueous solution comprising the inorganic base and the water miscible solvent, a catalytic amount of phase transfer catalyst is used in a method of the present invention. One of ordinary skill in the art would understand what is meant by a catalytic amount, and that a catalytic amount of a particular reagent will vary depending on the amounts of other reagents in the reaction. Determining a catalytic amount of a phase transfer catalyst to be used in a method of the present invention is well within the skill level of the ordinary artisan in view of the present disclosure.

In some embodiments of the present invention, the aqueous solution can further comprise a water immiscible organic solvent, which can be the same as or different from the water immiscible organic solvent used in the solution containing the N-methyl-N-nitroso amine compound. Preferably, when an aqueous solution further comprises a water immiscible organic solvent, it is the same water immiscible organic solvent as that in the N-methyl-N-nitroso amine solution.

According to embodiments of the present invention, while adding the solution of the N-methyl-N-nitroso amine of formula (IV) to the aqueous solution, the aqueous solution is maintained at a temperature sufficient to vaporize the water immiscible organic solvent and the diazomethane that is formed. Diazomethane is a gas at room temperature and condenses to the liquid phase at a temperature of about −23° C. The concentration of N-methyl-N-nitroso amine in the water immiscible organic solvent, concentration of inorganic base in the aqueous solution, temperature of the aqueous solution, and rate of addition of the solution containing the N-methyl-N-nitroso amine to the aqueous solution are adjusted accordingly to control the production of diazomethane, such that the amount of diazomethane in both the vapor and liquid phases is limited to a non-explosive level.

According to embodiments of the present invention, the concentration of N-methyl-N-nitroso amine in the water immiscible organic solvent is approximately 20% by weight. Preferably, the concentrations of the N-methyl-N-nitroso amine and inorganic base in the starting solutions, temperature of the aqueous solution, and rate of addition are selected such that the concentration of diazomethane does not exceed 3 percent by weight in the liquid phase, and 25 percent by volume in the vapor phase. For example, the concentration of diazomethane in the liquid phase can be 0.5%, 1%, 1.5%, 2%, 2.5% or 3% by weight, and the concentration of diazomethane in the vapor phase can be 15%, 16%, 17%, 18%, 19%, 20%, 21%, 22%, 23%, 24% or 25% by volume. Preferably, the concentration of diazomethane in the vapor phase is between 15% and 25% by volume.

According to embodiments of the present invention, the temperature of the aqueous solution is maintained at about 45° C. to about 55° C., and preferably at about 48° C. to about 53° C.

According to other embodiments, the concentration of the N-methyl-N-nitroso amine in the water immiscible organic solvent can be about 15 mol % to about 30 mol %, and the concentration of the inorganic base in the aqueous solution can be about 40 mol % to about 50 mol %.

The rate of addition of the solution of the N-methyl-nitroso amine in the water immiscible organic solvent to the aqueous solution of the inorganic base is adjusted to control the amount of diazomethane produced. According to embodiments of the present invention the rate of addition of the N-methyl-nitroso amine in the water immiscible organic solvent to the aqueous solution of the inorganic base is performed at a rate to meet all safety requirements when generating diazomethane, e.g., the condenser for isolating diazomethane is preferably maintained at <30° C., and addition is slow so as not to generate excess $N_2$ gas and pressurize the equipment. According to embodiments of the present invention, upon adding the solution of N-methyl-N-nitroso amine in the water immiscible organic solvent to the aqueous solution of the inorganic base and water miscible solvent, diazomethane is vaporized along with the water immiscible organic solvent, providing a vapor phase. The vapor phase, which contains diazomethane, is then condensed to liquid form. Preferably, once the vapor phase is condensed to liquid form, the concentration of diazomethane in the liquid form does not exceed 40 mol % by weight. Once diazomethane is condensed into liquid form, the diazomethane can be reacted with a substantially pure d-threo stereoisomer of ritalinic acid represented by formula (II) or a salt thereof represented by formula (II-a). Moreover, the amount of water immiscible solvent distilled with the diazomethane can be varied to control the rate of reaction of diazomethane with the d-threo stereoisomer of ritalinic acid. For example, increasing the amount of water immiscible solvent will decrease the reaction rate.

According to embodiments of the present invention, the vapor phase containing diazomethane is condensed to the liquid phase at a temperature of about −22° C., and preferably at a temperature below −22° C., to about 15° C. The temperature over the course of distillation can vary. For example, at the start of distillation, the temperature is preferably below −22° C., but as the distillation continues the temperature can increase up to about 15° C. Once distillation is complete and the distillate containing diazomethane is collected, the diazomethane can be reacted with a substantially pure d-threo stereoisomer of ritalinic acid represented by formula (II) or a salt thereof represented by formula (II-a).

According to embodiments of the present invention, a substantially pure d-threo stereoisomer of ritalinic acid of formula (II) or a salt thereof of formula (II-a) that is in solution is mixed with a solvent that is inert to diazomethane, i.e., does not react with diazomethane, such as ethyl acetate. Preferably, the solvent is ethyl acetate.

In a preferred embodiment, the vapor phase containing diazomethane is condensed directly into a solution of a substantially pure d-threo stereoisomer of ritalinic acid of formula (II) or a salt thereof of formula (II-a). According to this embodiment, the temperature of the solution containing the substantially pure d-threo stereoisomer of ritalinic acid represented by formula (II) or salt thereof of formula (II-a) is initially maintained at a temperature of about −22° C. to about 15° C. to facilitate condensation of the vapor phase, and preferably, the temperature at the start of condensation is below −22° C. Upon completion of distillate collection, the temperature of the solution can then be increased to a temperature at which the diazomethane will react with the substantially pure d-threo stereoisomer of ritalinic acid represented by formula (II) or salt thereof represented by formula (II-a).

The starting material employed in a method of the present invention is a substantially pure d-threo stereoisomer of ritalinic acid represented by formula (II), or a salt thereof represented by formula (II-a), meaning that the ritalinic acid or salt thereof is substantially free of any l-threo, d-erythro, and l-erythro stereoisomers of the compound of formula (II). It is preferable that the salt of the substantially pure d-threo stereoisomer of ritalinic acid represented by formula (II) is 99% pure, and more preferably 99.9% pure or greater, meaning that no more than 0.1 to 1% of the compound of formula (II), and preferably no more than 0.01% to 0.1% is present in a stereoisomeric form other than the d-threo form as determined by high performance liquid chromatography (HPLC) analysis.

According to embodiments of the present invention, approximately 4 to 9 molar equivalents of diazomethane relative to the substantially pure d-threo stereoisomer of ritalinic acid represented by formula (II) or salt thereof of formula (II-a) are employed in a method of the present invention. For example, 4, 5, 6, 7, 8, or 9 molar equivalents of diazomethane can be used. In a preferred embodiment, approximately 4 molar equivalents of diazomethane are used.

According to embodiments of the present invention, a reaction of a substantially pure d-threo stereoisomer of ritalinic acid represented by formula (II) or salt thereof of formula (II-a) with diazomethane is performed at a temperature of about −20° C. to 10° C., and preferably at a temperature of about 10° C. During the course of the reaction, the reaction mixture can be stirred or agitated using any technique known in the art, and can proceed until the reaction between diazomethane and the substantially pure d-threo stereoisomer of ritalinic acid represented by formula (II) or salt thereof of formula (II-a) is complete. One of ordinary skill in the art would readily be able to determine when the reaction is complete by, for example, thin layer chromatography (TLC) analysis, etc. in view of the present disclosure For example, the reaction can be considered complete when approximately 90% of the ritalinic acid of formula (II) is converted to the compound of formula (I).

Preferably, the reaction mixture is stirred for a period of about 12 hours, and more preferably is stirred for a period of about 12 hours at a temperature of about 10° C.

Once the reaction is complete, the substantially pure d-threo stereoisomer of methylphenidate represented by formula (I) or salt thereof of formula (I-a) can be recovered from the reaction mixture. Methods for recovering the compound from the reaction mixture are not particularly limited, and any method known in the art can be used to isolate the compound, such as distillation, filtration, crystallization, precipitation, etc. For example, the reaction can be quenched with acid, followed by distillation to remove volatile organic solvents. The remaining solution can then be filtered, followed by the addition of hydrochloric acid to the filtrate to precipitate the substantially pure d-threo stereoisomer of methylphenidate represented by formula (I) or salt thereof of formula (I-a) as a solid. The solid containing the substantially pure d-threo stereoisomer of methylphenidate represented by formula (I) or salt thereof of formula (I-a) can be filtered, washed and dried. One of ordinary skill in the art will readily be able to determine and employ the appropriate techniques for recovering a substantially pure d-threo stereoisomer of methylphenidate represented by formula (I) or salt thereof of formula (I-a) from the reaction mixture in order to maximize compound yield, purity, etc.

According to embodiments of the present invention, upon completion of the reaction of diazomethane with the substantially pure d-threo stereoisomer of ritalinic acid represented by formula (II) or salt thereof of formula (II-a), any remaining diazomethane can be destroyed and rendered innocuous by the addition of an acid, preferably an organic acid, to liberate nitrogen and methyl compounds. A preferred organic acid for this purpose is acetic acid.

According to a preferred embodiment of the present invention, in a salt of a substantially pure d-threo stereoisomer of methylphenidate represented by formula (I-a), and a salt of a substantially pure d-threo stereoisomer of ritalinic acid represented by formula (II-a), X is chlorine.

According to embodiments of the present invention, a salt of a substantially pure d-threo stereoisomer of methylphenidate represented by formula (I-a) can be converted to any other salt using any method known in the art in view of the present disclosure. For example, when X is other than chlorine, the salt of the substantially pure d-threo stereoisomer of methylphenidate represented by formula (I-a) can be converted to substantially pure d-threo methylphenidate hydrochloride by, e.g., reacting the salt of methylphenidate with HCl.

In another general aspect, the present invention provides a method for preparing substantially pure d-threo-methylphenidate hydrochloride. d-threo-methylphenidate hydrochloride is a representative compound of formula (I-a), wherein X is chlorine and $R^1$ is a phenyl group.

According to embodiments of the present invention, the method comprises reacting substantially pure d-threo-ritalinic acid hydrochloride with diazomethane. Any method described herein for obtaining diazomethane can be used in a method for producing substantially pure d-threo-methylphenidate hydrochloride according to the invention.

d-threo-ritalinic acid hydrochloride is a representative compound of formula (II-a), wherein X is chlorine and $R_1$ is a phenyl group. d-threo-ritalinic acid hydrochloride has the following chemical structure:

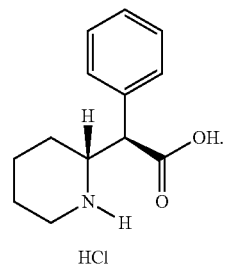 [SMILES: O=C(O)[C@H](c1ccccc1)[C@H]1CCCCN1 ; Cl]

d-threo-ritalinic acid hydrochloride for use in a method of the present invention can be obtained from a commercial source, or it can be obtained using any preparation method known in the art. For example, d-threo-ritalinic acid hydrochloride is commercially available from Malladi Drugs & Pharmaceuticals, Ltd.

According to embodiments of the present invention, d-threo ritalinic acid hydrochloride employed as starting material is substantially free of any l-threo, d-erythro, and l-erythro stereoisomers of ritalinic acid. It is preferable that the substantially pure d-threo-ritalinic acid hydrochloride be 99% pure, and more preferably 99.9% pure or more, meaning that no more than 0.1% to 1%, and preferably no more than 0.01% to 0.1%, of the ritalinic acid hydrochloride is present in a stereoisomeric form other than the d-threo form.

A method for producing substantially pure d-threo-methylphenidate hydrochloride by reacting substantially pure d-threo-ritalinic acid hydrochloride with diazomethane according to embodiments of the present invention is depicted in Scheme 3 below.

Scheme 3: Production of substantially d-threo-methylphenidate hydrochloride by reacting substantially pure d-threo-ritalinic acid hydrochloride with diazomethane.

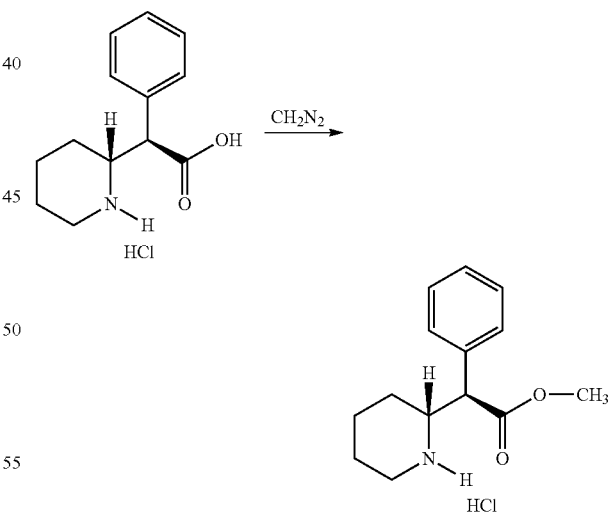

According to embodiments of the present invention, a method for preparing substantially pure d-threo-methylphenidate hydrochloride comprises obtaining a first solution comprising an aqueous solution of an inorganic base and a water miscible solvent, obtaining a second solution comprising an N-methyl-N-nitroso amine of formula (IV) in a water immiscible organic solvent, and adding the second solution to the first solution to generate diazomethane. The diazomethane that is generated is subsequently reacted with substantially pure d-threo-ritalinic acid hydrochloride, thereby producing substantially pure d-threo-methylphenidate hydrochloride.

Any of the reaction conditions, parameters, etc., described herein for a method of preparing a substantially pure d-threo stereoisomer of methylphenidate represented by formula (I) or a salt thereof represented by formula (I-a) can be used in a method according to the invention for preparing substantially pure d-threo-methylphenidate hydrochloride.

In a preferred embodiment of the present invention, a first solution comprises an aqueous solution of potassium hydroxide. In another preferred embodiment, the water immiscible organic solvent in the second solution is an ether solvent, preferably diethyl ether.

Until now, production of methylphenidate in both stereoisomerically pure form and in large quantities has been limited due to the need to purify the desired stereoisomer from a mixture of stereoisomers by recrystallization, for example, or due to synthetic procedures requiring a large number of steps, with a loss in product yield occurring at each step. Methods according to the present invention satisfy the need for a method that provides a substantially pure d-threo stereoisomer of methylphenidate in both pure stereoisomeric form and in large quantities. This is at least because a method according to the present invention utilizes a stereoisomerically pure starting material directly in a reaction that can be performed on a large scale. In a particularly preferred embodiment, substantially pure d-threo-methylphenidate hydrochloride can be produced by a method according to the present invention in both pure stereoisomeric form and in large quantities from a single reaction.

As used herein, in one embodiment, a reaction performed on "a large scale" or "a large scale reaction" is intended to mean a reaction that employs at least 300 grams of a substantially pure d-threo stereoisomer of ritalinic acid represented by formula (II) or a salt thereof of formula (II-a) as starting material per batch reaction. For example, at least 300, 400, 500, 600, 700, 800, 900 or 1000 grams or more of the substantially pure d-threo stereoisomer of ritalinic acid represented by formula (II) can be used as starting material. More preferably, a method according to the present invention is performed on a kilogram scale, wherein at least 1 kilogram of the substantially pure d-threo stereoisomer of ritalinic acid represented by formula (II) or salt thereof of formula (II-a) is used as starting material.

"Batch reaction," as used herein, has its broadest reasonable meaning as known in the art, and broadly refers to any reaction, wherein a predetermined amount of at least one reagent is added to the reaction at a particular rate of addition. In one embodiment, a "batch reaction" refers to a reaction, wherein a predetermined amount of a solution of an N-methyl-N-nitroso amine of formula (IV) in a water immiscible organic solvent is added to a solution comprising an aqueous solution of an inorganic base and a water miscible solvent to generate diazomethane, which can react with a substantially pure d-threo stereoisomer of ritalinic acid represented by formula (II) or a salt thereof of formula (II-a) to produce a substantially pure d-threo stereoisomer of methylphenidate of formula (I) or a salt thereof of formula (I-a). In another embodiment, a "batch reaction" refers to a reaction, wherein a predetermined amount of a solution of an N-methyl-N-nitroso amine of formula (IV) in a water immiscible organic solvent is added to a solution comprising an aqueous solution of an inorganic base and a water miscible solvent to generate diazomethane, which can react with substantially pure d-threo ritalinic acid hydrochloride to produce substantially pure d-threo methylphenidate hydrochloride.

In other embodiments, a reaction performed on "a large scale" or "a large scale reaction" refers to a reaction, wherein at least 200 grams of a substantially pure d-threo stereoisomer of methylphenidate represented by formula (I) or salt thereof of formula (I-a) is produced by a method of the present invention per batch reaction. For example, at least 200, 300, 400, 500, 600, 700, 800, or 900 grams or more of a substantially pure d-threo stereoisomer of methylphenidate represented by formula (I) or salt thereof of formula (I-a) can be produced by a method of the present invention per batch reaction.

In particularly preferred embodiments, at least 300 grams of substantially pure d-threo-ritalinic acid hydrochloride is used as starting material in a method of the present invention per batch reaction, such as 300, 400, 500, 600, 700, 800, 900 or 1000 grams or more per batch reaction. More preferably at least 1000 grams of substantially pure d-threo-ritalinic acid hydrochloride is utilized as starting material per batch reaction. Preferably, at least 200 grams of substantially pure d-threo-methylphenidate hydrochloride are produced by a method of the present invention per batch reaction.

The present inventors have also found that direct utilization of the hydrochloride salt of substantially pure d-threo-ritalinic acid in a method of the present invention enables high-throughput synthesis and manufacturing of d-threo methylphenidate hydrochloride that is more cost effective and can be more efficiently scaled-up. Methylphenidate hydrochloride (d-threo stereoisomer) is the approved active pharmaceutical ingredient (API) for the treatment of neurological disorders, e.g., attention deficit hyperactivity disorder (ADHD). Thus, by using the hydrochloride salt of d-threo ritalinic acid in a method of the present invention, the API can be obtained directly, thereby eliminating additional synthetic steps that would otherwise be necessary to obtain the hydrochloride salt, e.g., conversion to free base, reaction with HCl, etc.

Another general aspect of the present invention provides a system for producing a substantially pure d-threo stereoisomer of methylphenidate represented by formula (I) or a salt thereof of formula (I-a). According to embodiments of the present invention, a system comprises (i) a reaction chamber comprising a generator portion and a receiver portion, and (ii) a solution of an N-methyl-N-nitroso amine of formula (IV) in a water immiscible organic solvent.

According to embodiments of the present invention, the generator portion comprises an inlet. The inlet can be of any size and shape, and can be located anywhere on the generator portion, so long as the inlet allows for the introduction of the solution of the N-methyl-N-nitroso amine of formula (IV) into the generator portion. The generator portion holds an aqueous solution comprising an inorganic base and a water miscible solvent. Any inorganic base disclosed herein can be used. Preferably, the inorganic base is potassium hydroxide.

The generator portion is maintained at a temperature sufficient to vaporize the water immiscible organic solvent and the diazomethane that is generated upon introduction of the N-methyl-N-nitroso amine of formula (IV) into the generator portion. The temperature of the generator portion is maintained at a temperature of about 45° C. to about 55° C., and preferably at temperature of about 48° C. to about 53° C.

According to embodiments of the present invention, the receiver portion is connected to the generator portion by a condenser. The condenser is maintained at a temperature that facilitates condensation of the vapor phase containing diazomethane and the water immiscible organic solvent. The condenser is maintained at a temperature of about −22° C. to about 15° C., and is more preferably maintained at a temperature below −22° C. at least at the start of distillation.

The receiver portion holds a substantially pure d-threo stereoisomer of ritalinic acid represented by formula (II) or a salt thereof of formula (II-a). Preferably, the substantially pure d-threo stereoisomer of ritalinic acid or salt thereof is in solution, and is more preferably in a solution of ethyl acetate. The temperature at which the receiver portion is maintained is variable, and can be adjusted depending upon which step of the method is being performed. For example, during the generation of diazomethane, wherein the solution containing the N-methyl-N-nitroso amine of formula (IV) in a water immiscible organic solvent is being fed into the generator portion via the inlet to produce diazomethane, the receiver portion is maintained at a temperature that facilitates condensation of the vapor phase, such that the distillate is collected in the receiver portion. During this stage of the method, the temperature of the receiver portion is preferably maintained at about −22° C. to about 15° C., and preferably below about −22° C. at least at the start of distillation. In a particularly preferred embodiment, the receiver portion at this stage is maintained at temperature that is substantially equivalent to the temperature at which the condenser is maintained. However, once collection of the distillate in the receiver portion is complete, the temperature of the receiver portion can be adjusted to a temperature that promotes the reaction of diazomethane with the substantially pure d-threo stereoisomer of ritalinic acid of formula (II) or salt thereof of formula (II-a), such as, for example, about 10° C.

Any of the methods for producing a substantially pure d-threo stereoisomer of methylphenidate of formula (I) or salt thereof of formula (I-a), or for producing substantially pure d-threo-methylphenidate hydrochloride described herein can be performed using a system according to the present invention. A system according to the present invention allows for diazomethane to be used directly in a method of the present invention as soon as it is generated.

The inventors of the present invention have surprisingly discovered that upon reacting a salt of a substantially pure d-threo stereoisomer of ritalinic acid represented by formula (II-a) with diazomethane to produce a salt of a substantially pure d-threo-stereoisomer of methylphenidate represented by formula (I-a) according to a method of the present invention, an N-methyl species of the d-threo stereoisomer of methylphenidate represented by formula (I) having the following formula (III) is also obtained:

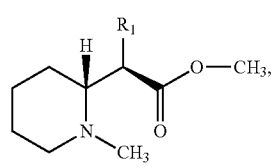

(III)

wherein $R_1$ represents a phenyl group.

Likewise, upon reacting substantially pure d-threo-ritalinic acid hydrochloride with diazomethane to produce substantially pure d-threo-methylphenidate hydrochloride, an N-methyl species of d-threo-methylphenidate hydrochloride is also produced having the above formula (III), wherein $R_1$ represents a phenyl group is also obtained. This was a surprising effect of the present invention because diazomethane is typically not known to methylate the nitrogen atom of a piperidine moiety. Without wishing to be bound by any theories, it is believed that formation of the N-methyl species can be produced upon a reaction with, e.g., methyl chloride. The methyl chloride is believed to be produced from a reaction of diazomethane with d-threo ritalinic acid hydrochloride.

According to embodiments of the present invention, in a method for producing a substantially pure d-threo stereoisomer of methylphenidate or salt thereof, an N-methyl species represented by formula (III) is produced in an amount that is about 5% to 8% by area based on peak area of a peak corresponding to the N-methyl species as determined by high performance liquid chromatography (HPLC) analysis, and preferably 5% area or less, relative to a total of 100% area based on peak area of peaks corresponding to the substantially pure d-threo stereoisomer of methylphenidate or salt thereof and the N-methyl species of formula (III) as determined by HPLC analysis. For example, the N-methyl species of formula (III) is produced in an amount that is about 8%, 7%, 6%, 5%, 4%, 3%, 2%, 1%, 0.5% 0.4%, 0.3%, 0.2%, 0.1% area or less, based on the area of the peak corresponding to the N-methyl species of formula (III) relative to the total area of the peaks corresponding to the N-methyl species of formula (III) and the substantially pure d-threo stereoisomer of methylphenidate or salt thereof as determined by HPLC analysis.

According to another preferred embodiment of the present invention, in a method for producing substantially pure d-threo-methylphenidate hydrochloride, an N-methyl species thereof is produced in an amount that is about 5% to 8% area based on a peak area corresponding to the N-methyl species, and preferably 5% area or less, relative to a total of 100% area based on peak area of peaks corresponding to the substantially pure d-threo-methylphenidate hydrochloride and the N-methyl species thereof as determined by HPLC analysis. For example, the N-methyl species is produced in an amount that is about 8%, 7%, 6%, 5%, 4%, 3%, 2%, 1%, 0.5%, 0.4%, 0.3%, 0.2%, 0.1% area or less based on the area of the peak corresponding to the N-methyl species relative to the total area of the peaks corresponding to the N-methyl species and the substantially pure d-threo-methylphenidate hydrochloride as determined by high performance liquid chromatography (HPLC) analysis.

A substantially pure d-threo-stereoisomer of methylphenidate represented by formula (I) or a salt thereof of formula (I-a) produced according to a method of the present invention can be purified to remove any N-methyl species of formula (III) by any method known in the art for purifying chemical compounds. For example, the salt of the substantially pure d-threo-stereoisomer of methylphenidate represented by formula (I-a) can be separated from the N-methyl species of formula (III) by washing with a mixture of isopropyl acetate/acetone. As another illustrative example, addition of stoichiometric amounts of hydrochloric acid to form the hydrochloride salt of the substantially pure d-threo-stereoisomer of methylphenidate represented by formula (I) can be used as a method for purifying away the N-methyl species thereof. Thus, a method according to an embodiment of the present invention further comprises separating the substantially pure d-threo-stereoisomer of methylphenidate of formula (I) or salt thereof of formula (I-a) from the N-methyl species thereof.

In a preferred embodiment, a substantially pure d-threo stereoisomer of methylphenidate represented by formula (I) or salt thereof represented by formula (I-a) produced according to a method of the present invention contains no more than 0.10% of the N-methyl species.

In another aspect, the present invention relates to a composition comprising a pharmaceutically acceptable salt of substantially pure d-threo methylphenidate hydrochloride, and an N-methyl species of d-threo methylphenidate hydrochloride.

According to embodiments of the present invention, substantially pure d-threo methylphenidate hydrochloride and the N-methyl species thereof in a composition of the present invention are obtained by a method according to the present invention for preparing substantially pure d-threo methylphenidate hydrochloride by reacting substantially pure d-threo ritalinic acid hydrochloride with diazomethane.

In a preferred embodiment, a composition according to the invention comprises substantially pure d-threo-methylphenidate hydrochloride and an N-methyl species of d-threo-methylphenidate hydrochloride, wherein the N-methyl species is present in an amount that is no more than 0.10% area based on peak area as determined by HPLC analysis relative to a total of 100% area based peak area of peaks corresponding to the substantially pure d-threo methylphenidate hydrochloride and the N-methyl species thereof. For example, the N-methyl species is present in an amount that is 0.10%, 0.09%, 0.08%, 0.07%, 0.06%, 0.05%, 0.01%, 0.001% area or less.

The following examples of methods for preparing a salt of a substantially pure d-threo stereoisomer of methylphenidate represented by formula (I) according to embodiments of the present invention are to further illustrate the nature of the invention. It should be understood that the following examples do not limit the invention and that the scope of the invention is to be determined by the appended claims.

EXAMPLES

The following abbreviations are used in the following examples, unless clearly stated otherwise:

iProAc: isopropyl acetate
HPLC: high performance liquid chromatography
g: grams
mol: moles
S: weight equivalents of material relative to equivalents of starting material
S.M.: starting material
d-TRA-HCl: d-threo-ritalinic acid hydrochloride
d-TRA-HBF$_4$: d-threo-ritalinic acid tetrafluoroboric acid
THF: tetrahydrofuran
EtOAc: ethyl acetate
Et$_2$O: diethyl ether
R.T. reaction temperature

Example 1

Preparation of D-Threo-Methylphenidate Hydrochloride from D-Threo-Ritalinic Acid Hydrochloride using Diazomethane d-threo-ritalinic acid hydrochloride (10 g, 0.04 mol, 1S) was added to the receiver portion of a reaction cell, followed by the addition of ethyl acetate (180 g, 18 S). The solution containing d-threo-ritalinic acid hydrochloride was then cooled to −20° C. In the generator portion of the reaction cell, 45% potassium hydroxide solution (30 g, 3S), diethylene glycol monoethyl ether (59 g, 5.9 S) and diethyl ether (5 g, 0.5 S) were charged and heated to a temperature that was maintained between to 48° C. to 53° C.

Separately, a diazald solution in ether was prepared (approx 26 wt %, 140 g, 14 S). The diazald solution was then fed into the generator, with the temperature maintained at a range of 48° C. to 53° C. The distillate was collected in the receiver, with the temperature of the receiver maintained at −15° C. to −22° C. during collection of the distillate.

After collection of the distillate was complete, the receiver was heated to 10° C. and post-stirred for 12 hours. The reaction was quenched by adding 60% acetic acid (4 g) to the receiver, maintaining the temperature at 10° C. (~80% conversion was observed in process). The quenched reaction solution was vacuum distilled at ambient temperature to remove diethyl ether until approximately 110 g (11 S) of solution remained. The mother liquor was filtered to remove unreacted d-threo-ritalinic acid hydrochloride (approximately 2 g wet, 0.2 S). The filtrate was cooled down to between 0° C.-5° C., and charged with 37% aqueous hydrochloric acid (2.70 g, 0.27 S) to precipitate solids. The precipitated solids were filtered and washed with a mixture of iProAc (5 g, 0.5 S) and acetone (27 g, 2.7 S) until an in process sample contained no less than 99.5% of d-threo-methylphenidate hydrochloride and not more than any unknown of 0.10%. The product was dried under vacuum at 45° C. until a constant weight was achieved (approximately 12 h). Expected yield 76%; HPLC Purity 99.7% area. Actual yield 85.7% yield; HPLC purity 99.92% area.

Example 2

Preparation of a Salt, Including the Hydrochloride Salt, of a Substantially Pure D-Threo Stereoisomer of Methylphenidate from a Salt of Substantially Pure D-Threo Stereoisomer of Ritalinic Acid A salt of d-threo-methylphenidate was prepared according to methods of the present invention by reacting a salt of d-threo-ritalinic acid with diazomethane. The salt of d-threo-ritalinic acid used as starting material, equivalents of diazomethane, initial reaction temperature, final reaction temperature and reaction time, and solvent were varied, as detailed below in Table 1. Reactions were carried out as described in Example 1.

TABLE 1

Summary of reactions to produce d-threo-methylphenidate by reacting d-threo-ritalinic acid with diazomethane.

| Reaction No. | S.M.[1] | Scale (g) | Solvent | CH$_2$N$_2$ Equiv. | Initial R.T. (° C.) | Final R.T. (° C.) | Reaction Time | % AUC[3] N-methyl formed | Yield[2] (%) |
|---|---|---|---|---|---|---|---|---|---|
| 1 | d-TRA-HCl | 0.1 | EtOAc | 3 | −38.1 | Room temp. | overnight | n.i.[4] | n.i. |

TABLE 1-continued

Summary of reactions to produce d-threo-methylphenidate
by reacting d-threo-ritalinic acid with diazomethane.

| Reaction No. | S.M.[1] | Scale (g) | Solvent | $CH_2N_2$ Equiv. | Initial R.T. (°C.) | Final R.T. (°C.) | Reaction Time | % AUC[3] N-methyl formed | Yield[2] (%) |
|---|---|---|---|---|---|---|---|---|---|
| 2 | d-TRA-HCl | 0.1 | EtOAc | 6 | −38.1 | Room temp. | Overnight | n.i. | n.i. |
| 3 | d-TRA-HCl | 0.1 | EtOAc | 9 | −38.1 | Room temp. | overnight | n.i. | n.i. |
| 4 | d-TRA-HCl | 0.1 | EtOAc | 1 | −35 | Room temp. | overnight | n.i. | n.i. |
| 5 | d-TRA-HCl | 0.1 | EtOAc | 2 | −35 | Room temp. | overnight | n.i. | n.i. |
| 6 | d-TRA-HCl | 0.1 | EtOAc | 3 | −35 | Room temp. | overnight | n.i. | n.i. |
| 7 | d-TRA-HCl | 0.1 | EtOAc | 1 | −30.1 | 0 | 1.5 h | aq.[5] | n.i. |
| 8 | d-TRA-HCl | 0.1 | EtOAc | 2 | −30.1 | 0 | 1.5 h | aq. | n.i. |
| 9 | d-TRA-HCl | 0.1 | EtOAc | 3 | −30.1 | 0 | 1.5 h | aq. | n.i. |
| 10 | d-TRA-HCl | 0.1 | EtOAc | 1 | −35.2 | 10 | 2 h 16 min | 0.70 | n.i. |
| 11 | d-TRA-HCl | 0.1 | EtOAc | 2 | −35.2 | 10 | 2 h 16 min | 1.40 | n.i. |
| 12 | d-TRA-HCl | 0.1 | EtOAc | 3 | −35.2 | 10 | 2 h 16 min | 7.90 | n.i. |
| 13 | d-TRA-HCl | 0.1 | EtOAc | 4 | −61.7 | 5.6 | 1.5 h | 2.2 | n.i. |
| 14 | d-TRA-HCl | 0.1 | EtOAc | 5 | −61.7 | 5.6 | 1.5 h | 0.10 | n.i. |
| 15 | d-TRA-HBF$_4$ | 0.1 | EtOAc | 3 | −61.7 | 5.6 | 1.5 h | 11.6 | n.i. |
| 16 | d-TRA-HBF$_4$ | 0.1 | EtOAc | 0.5 | −24 | 2.8 | 1.5 h | 3.4 | n.i. |
| 17 | d-TRA-HBF$_4$ | 0.1 | EtOAc | 1 | −24 | 2.8 | 1.5 h | 1.30 | n.i. |
| 18 | d-TRA-HBF$_4$ | 0.1 | EtOAc | 1.5 | −24 | 2.8 | 1.5 h | 1.90 | n.i. |
| 19 | d-TRA-HCl | 0.1 | EtOAc | 4 | −60.1 | −9.9 | 1 h | 2.74 | n.i. |
| 20 | d-TRA-HCl | 0.1 | THF | 4 | −60.1 | −9.9 | 1 h | 2.31 | n.i. |
| 21 | d-TRA-HCl | 0.1 | Et$_2$O | 4 | −60.1 | −9.9 | 1 h | 2.12 | n.i. |
| 22 | d-TRA-HCl | 20 | THF | 4 | −45 | 10 | 6.5 | 10.27 | 34 |
| 23 | d-TRA-HCl | 10 | EtOAc | 4 | −20 | 10 | 5 | 4.8 | 76 (wet) |
| 24 | d-TRA-HCl | 10 | EtOAc | 4 | −20 | 11.6 | 11 | 5.42 | n.i. |
| 25 | d-TRA-HCl | 10 | EtOAc | 4 | −27 | 11 | 6.5 | 6.01 | n.i. |
| 26 | d-TRA-HCl | 10 | EtOAc | 4 | −15 | 10 | 7 | 5.66 | 39.8 |
| 27 | d-TRA-HCl | 10 | EtOAc | 4 | −14 | 10 | 5 | 5.93 | 78.8 |
| 28 | d-TRA-HCl | 10 | EtOAc | 4 | −32 | 13 | 8 | 4.54 | 63.8 |
| 29 | d-TRA-HCl | 10 | EtOAc | 4 | −20.8 | 14 | overnight | 5.7 | 84.8 |
| 30 | d-TRA | 0.1 | EtOAc | 3 | −38.1 | Room temp. | overnight | 1.7 | n.i. |
| 31 | d-TRA | 0.1 | EtOAc | 6 | −38.1 | Room temp. | overnight | 2.4 | n.i. |
| 32 | d-TRA | 0.1 | EtOAc | 9 | −38.1 | Room temp. | overnight | 4.6 | n.i. |

[1] d-TRA-HCl refers to d-threo-ritalinic acid hydrochloride; d-TRA-HBF$_4$ refers to d-threo-ritalinic acid tetrafluoroboric acid.
[2] Yield refers to the total amount of methyl ester product.
[3] % AUC refers to percent area under the curve determined by HPLC analysis and is reported as area % (uncorrected)(% AUC).
[4] "n.i." means that the species was not identified by the detection method employed.
[5] "a.q." indicates that the N-methyl species was identified in aqueous streams upon work-up of the reaction.

The results demonstrate that substantially pure d-threo methylphenidate hydrochloride can be prepared in good yield and by reaction of substantially pure d-threo ritalinic acid hydrochloride with diazomethane.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition comprising substantially pure d-threo-methylphenidate hydrochloride and an N-methyl species of d-threo-methylphenidate hydrochloride having the formula (III):

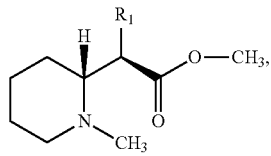

(III)

wherein $R_1$ represents phenyl.

2. The composition according to claim 1, wherein the N-methyl species is present in an amount that is about 8% area or less based on peak area of a peak corresponding to the N-methyl species as determined by high performance liquid chromatography (HPLC) analysis relative to a total of 100% area based on peak area of peaks corresponding to the substantially pure d-threo-methylphenidate hydrochloride and N-methyl species thereof as determined by HPLC analysis.

3. The composition according to claim 2, wherein the N-methyl species is present in an amount that is about 5% area or less based on the peak area of the peak corresponding to the N-methyl species.

4. The composition according to claim 2, wherein the N-methyl species is present in an amount that is no more than 0.10% area based on the peak area of the peak corresponding to the N-methyl species.

5. The composition according to claim 1, wherein the N-methyl species is present in an amount ranging from about 0.001% area to about 8% area based on the peak area of the peak corresponding to the N-methyl species.

6. A composition comprising substantially pure d-threo-methylphenidate hydrochloride and an N-methyl species of d-threo-methylphenidate hydrochloride having the formula (III):

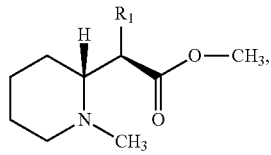

(III)

wherein the substantially pure d-threo-methylphenidate hydrochloride and the N-methyl species of d-threo-methylphenidate hydrochloride are obtained by a method comprising:

(i) obtaining a first solution comprising an aqueous solution of an inorganic base and a water miscible solvent;

(ii) obtaining a second solution comprising an N-methyl-N-nitroso amine of formula (IV):

(IV)

in a water immiscible organic solvent;

(iii) adding the second solution to the first solution, thereby generating diazomethane; and (iv) reacting substantially pure d-threo-ritalinic acid hydrochloride with the diazomethane generated in step (iii) for at least about five hours to obtain the substantially pure d-threo-methylphenidate hydrochloride, wherein the reaction is performed at a temperature of about −20° C. to about 10° C., and a molar ratio of diazomethane to the substantially pure d-threo stereoisomer of ritalinic acid hydrochloride is about 4 to 9, and wherein $R_1$ represents phenyl;

$R_2$ represents a member selected from the group consisting of:

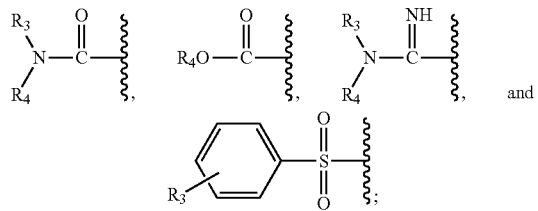

$R_3$ represents a hydrogen atom, an alkyl group having one to four carbon atoms, or a nitro group;

and $R_4$ represents a hydrogen atom or an alkyl group having one to four carbon atoms.

7. The composition according to claim 6, wherein the N-methyl species is present in an amount that is about 8% area or less based on peak area of a peak corresponding to the N-methyl species as determined by high performance liquid chromatography (HPLC) analysis relative to a total of 100% area based on peak area of peaks corresponding to the substantially pure d-threo-methylphenidate hydrochloride and N-methyl species thereof as determined by HPLC analysis.

8. The composition according to claim 7, wherein the N-methyl species is present in an amount that is about 5% area or less based on the peak area of the peak corresponding to the N-methyl species.

9. The composition according to claim 7, wherein the N-methyl species is present in an amount that is no more than 0.1% area based on the peak area of the peak corresponding to the N-methyl species.

10. The composition according to claim 6, wherein the N-methyl species is present in an amount ranging from about 0.001% area to about 8% area based on the peak area of the peak corresponding to the N-methyl species.

11. A system for producing the composition of claim 6, the system comprising:
(i) a reaction chamber comprising:
(a) a generator portion comprising an inlet, and holding the first solution comprising the aqueous solution of the inorganic base and the water miscible solvent, and
(b) a receiver portion connected to the generator portion by a condenser, the receiver portion holding the substantially pure d-threo-ritalinic acid hydrochloride; and
(ii) the second solution comprising the N-methyl-N-nitroso amine of formula (IV):

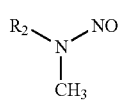

(IV)

in the water immiscible organic solvent,
wherein the generator portion is maintained at a temperature sufficient to vaporize the organic solvent and the diazomethane generated upon introduction of the second solution into the generator portion via the inlet, and the receiver portion receives the vaporized diazomethane and the receiver is maintained at the temperature of about −20° C. to about 10° C. for at least about five hours to obtain the substantially pure d-threo-methylphenidate hydrochloride.

12. A composition comprising substantially pure d-threo-methylphenidate hydrochloride and an N-methyl species of d-threo-methylphenidate hydrochloride having the formula (III):

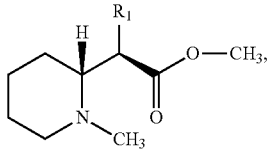

(III)

wherein the N-methyl species is present in an amount ranging from about 0.001% area to 0.10% area based on peak area of a peak corresponding to the N-methyl species as determined by high performance liquid chromatography (HPLC) analysis relative to a total of 100% area based on peak area of peaks corresponding to the substantially pure d-threo-methylphenidate hydrochloride and N-methyl species thereof as determined by HPLC analysis, and wherein $R_1$ represents phenyl.

13. The composition according to claim 12, wherein the substantially pure d-threo-methylphenidate hydrochloride and the N-methyl species of d-threo-methylphenidate hydrochloride are obtained by a method comprising:
(i) obtaining a first solution comprising an aqueous solution of an inorganic base and a water miscible solvent;
(ii) obtaining a second solution comprising an N-methyl-N-nitroso amine of formula (IV):

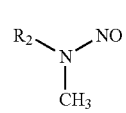

(IV)

in a water immiscible organic solvent;
(iii) adding the second solution to the first solution, thereby generating diazomethane; and
(iv) reacting substantially pure d-threo-ritalinic acid hydrochloride with the diazomethane generated in step (iii) for at least about five hours to obtain the substantially pure d-threo-methylphenidate hydrochloride,
wherein the reaction is performed at a temperature of about −20° C. to about 10° C., and a molar ratio of diazomethane to the substantially pure d-threo stereoisomer of ritalinic acid hydrochloride is about 4 to 9, and
wherein $R_2$ represents a member selected from the group consisting of

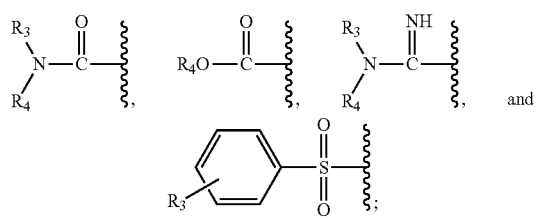

$R_3$ represents a hydrogen atom, an alkyl group having one to four carbon atoms, or a nitro group;
and $R_4$ represents a hydrogen atom or an alkyl group having one to four carbon atoms.

* * * * *